US012589003B2

(12) United States Patent
    Dusterhoft et al.

(10) Patent No.: US 12,589,003 B2
(45) Date of Patent: Mar. 31, 2026

(54) SPINAL INTERBODY SPACER

(71) Applicant: Astura Medical Inc., Iriving, TX (US)

(72) Inventors: Ross Dusterhoft, Irving, TX (US);
                Thomas Purcell, Irving, TX (US)

(73) Assignee: ASTURA MEDICAL INC, Irving, TX
              (US)

( * ) Notice: Subject to any disclaimer, the term of this
              patent is extended or adjusted under 35
              U.S.C. 154(b) by 105 days.

(21) Appl. No.: 18/215,825

(22) Filed: Jun. 29, 2023

(65) Prior Publication Data

US 2024/0000580 A1     Jan. 4, 2024

Related U.S. Application Data

(60) Provisional application No. 63/356,571, filed on Jun.
     29, 2022.

(51) Int. Cl.
     A61F 2/44              (2006.01)
(52) U.S. Cl.
     CPC ............. A61F 2/442 (2013.01); A61F 2/4455
                    (2013.01); A61F 2/447 (2013.01)
(58) Field of Classification Search
     CPC .......... A61F 2/44; A61F 2/442; A61F 2/4455;
                   A61F 2/446; A61F 2/4465; A61F 2/447;
                                        A61F 2002/444
     See application file for complete search history.

(56) References Cited

U.S. PATENT DOCUMENTS

| | | | |
|---|---|---|---|
| 8,308,774 B2 | 11/2012 | Hoffman et al. | |
| 9,364,342 B2 * | 6/2016 | Walkenhorst | ...... A61B 17/7059 |
| 9,370,435 B2 * | 6/2016 | Walkenhorst | ...... A61B 17/7059 |
| 9,649,139 B2 | 5/2017 | Sharifi-Mehr et al. | |
| 9,913,729 B2 * | 3/2018 | Walkenhorst | ......... A61F 2/4455 |
| 10,166,114 B2 * | 1/2019 | Fiechter | ................. A61F 2/4465 |
| 10,322,006 B2 * | 6/2019 | Bennett | .................... A61F 2/44 |
| 11,160,666 B2 * | 11/2021 | Burkhardt | ............. A61F 2/4455 |
| 11,273,049 B2 * | 3/2022 | Bennett | ............... A61F 2/30744 |
| 11,654,030 B2 * | 5/2023 | Valkoun | .................. A61F 2/447 |
| | | | 623/17.16 |
| 12,042,398 B2 * | 7/2024 | Bennett | ............... A61F 2/30744 |
| 12,245,951 B2 * | 3/2025 | Burkhardt | ............. A61F 2/4455 |
| 2012/0277867 A1 * | 11/2012 | Kana | ..................... A61F 2/4455 |
| | | | 623/17.16 |

(Continued)

FOREIGN PATENT DOCUMENTS

| | | | | | |
|---|---|---|---|---|---|
| AU | 2023300538 A1 * | 12/2024 | | ............. | A61F 2/442 |
| EP | 2628467 A1 * | 8/2013 | | ......... | A61F 2/30749 |

(Continued)

OTHER PUBLICATIONS

International Search Report for PCT Application No. PCT/US23/
16205 dated Jul. 7, 2023.

(Continued)

*Primary Examiner* — Eric S Gibson

(74) *Attorney, Agent, or Firm* — Michael R Shevlin

(57)                    ABSTRACT

Disclosed is a spinal interbody spacer that includes a spinal
spacer body with an asymmetrical open end, an asymmetri-
cal screw fixation plate configured to couple with the
asymmetrical open end, and a locking mechanism config-
ured to lock the screw fixation plate and the spinal spacer
body together.

14 Claims, 9 Drawing Sheets

(56) References Cited

U.S. PATENT DOCUMENTS

| | | | | |
|---|---|---|---|---|
| 2013/0345814 A1 * | 12/2013 | Walkenhorst | ...... | A61B 17/7059 |
| | | | | 623/17.16 |
| 2014/0039623 A1 * | 2/2014 | Iott | ........................ | A61F 2/447 |
| | | | | 623/17.16 |
| 2014/0228957 A1 * | 8/2014 | Niemiec | ............... | A61F 2/4455 |
| | | | | 623/17.16 |
| 2014/0277497 A1 * | 9/2014 | Bennett | ................. | A61F 2/4455 |
| | | | | 623/17.16 |
| 2014/0330386 A1 * | 11/2014 | Walkenhorst | ...... | A61B 17/7059 |
| | | | | 623/17.16 |
| 2015/0190241 A1 * | 7/2015 | Gowan | ................. | A61F 2/4455 |
| | | | | 623/17.16 |
| 2015/0374510 A1 * | 12/2015 | Fiechter | .............. | A61F 2/30749 |
| | | | | 623/17.16 |
| 2016/0081812 A1 * | 3/2016 | Waugh | ................. | A61F 2/4684 |
| | | | | 623/17.16 |
| 2016/0278821 A1 | 9/2016 | Artaki et al. | | |
| 2016/0324657 A1 * | 11/2016 | Walkenhorst | ......... | A61F 2/4465 |
| 2016/0338852 A1 * | 11/2016 | Walkenhorst | ...... | A61B 17/7059 |
| 2018/0147068 A1 * | 5/2018 | Walkenhorst | ......... | A61F 2/4455 |
| 2019/0254730 A1 | 8/2019 | Rohlfing et al. | | |
| 2019/0262142 A1 * | 8/2019 | Bennett | ............... | A61F 2/30744 |
| 2019/0336304 A1 * | 11/2019 | Burkhardt | ........... | A61F 2/30767 |
| 2020/0330239 A1 * | 10/2020 | Davenport | ............ | A61F 2/4455 |
| 2021/0145490 A1 | 5/2021 | Butler et al. | | |
| 2021/0369466 A1 * | 12/2021 | Valkoun | ................ | A61F 2/4455 |
| 2022/0151802 A1 * | 5/2022 | Bennett | ............... | A61F 2/30744 |
| 2024/0000580 A1 * | 1/2024 | Dusterhoft | ............ | A61F 2/4455 |
| 2024/0065853 A1 * | 2/2024 | Burkhardt | ............ | A61F 2/4611 |
| 2024/0374397 A1 * | 11/2024 | Bennett | ..................... | A61F 2/44 |

FOREIGN PATENT DOCUMENTS

| | | | | | |
|---|---|---|---|---|---|
| EP | 2628467 B1 * | 4/2017 | ........ | A61F 2/30749 |
| EP | 2779954 B1 * | 10/2018 | ........ | A61B 17/7059 |
| EP | 2956091 B1 * | 7/2019 | ........ | A61F 2/30749 |
| JP | 6928449 B2 * | 9/2021 | ........ | A61F 2/30744 |
| WO | WO-2013075124 A1 * | 5/2013 | ........ | A61B 17/7059 |
| WO | WO2014005154 A1 | 1/2014 | | |
| WO | WO-2014125428 A1 * | 8/2014 | ........ | A61F 2/30749 |
| WO | WO-2014151175 A1 * | 9/2014 | ........ | A61F 2/30744 |
| WO | WO-2014151175 A9 * | 5/2015 | ........ | A61F 2/30744 |
| WO | WO-2021062068 A1 * | 4/2021 | ........... | A61F 2/442 |
| WO | WO-2024006398 A1 * | 1/2024 | ........... | A61F 2/442 |

OTHER PUBLICATIONS

International Written Opinion for PCT Application No. PCT/US23/16205 dated Jul. 7, 2023.
International Search Report and Written Opinion in PCT Application No. PCT/US23/26513 dated Oct. 6, 2023.

* cited by examiner

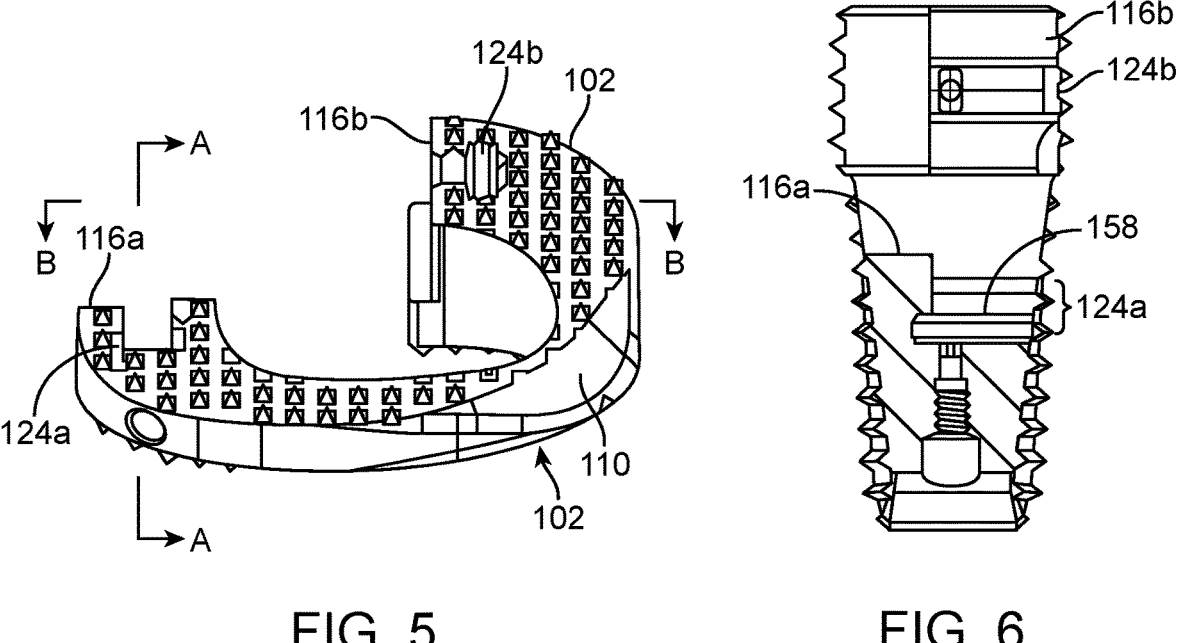
FIG. 5
FIG. 6
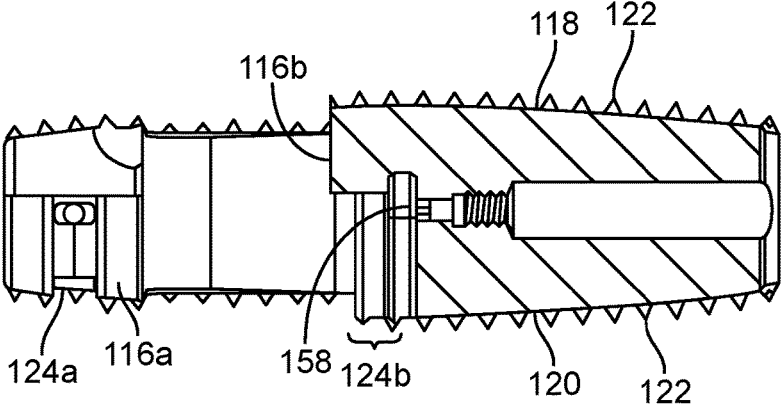
FIG. 7

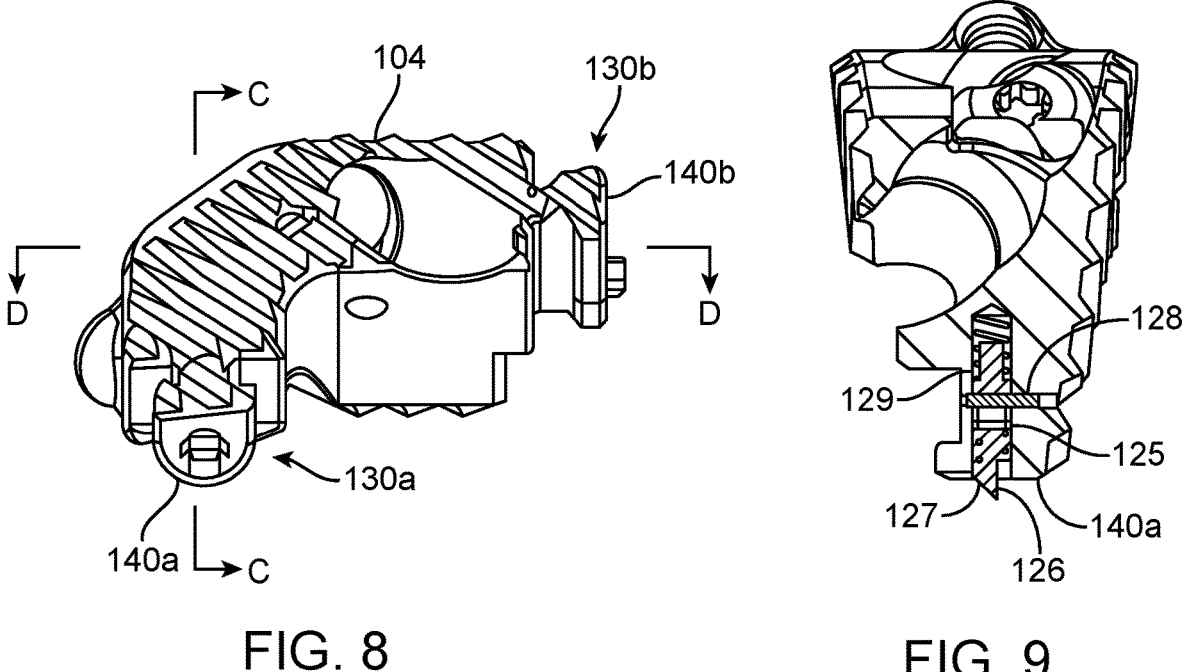
FIG. 8
FIG. 9
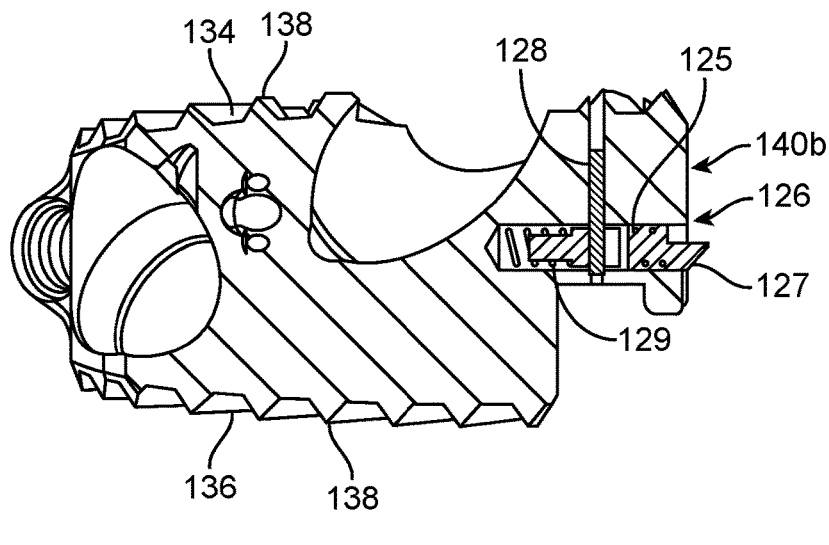
FIG. 10

SPINAL INTERBODY SPACER

CROSS-REFERENCE TO RELATED APPLICATIONS

This application claims the benefit of U.S. Provisional Application No. 63/356,571, filed Jun. 29, 2022 all of which are incorporated herein by reference. This application is related to U.S. patent application Ser. No. 17/031,885, filed Sep. 24, 2020, which claims the benefit of U.S. Provisional Application No. 62/905,384, filed Sep. 24, 2019, all of which are incorporated herein by reference.

FIELD

The present invention relates generally to the field of surgery, and more specifically, to a spinal interbody spacer for placement in intervertebral space between adjacent vertebrae during spinal fixation.

BACKGROUND

A spinal disc can become damaged as a result of degeneration, dysfunction, disease and/or trauma. Conservative treatment can include non-operative treatment through exercise and/or pain relievers to deal with the pain. Operative treatment options include disc removal and replacement using an interbody spacer such as anterior lumbar interbody fusion (ALIF), extreme lateral interbody fusion (XLIF), posterior lumbar interbody fusion (PLIF), transforaminal lumbar interbody fusion (TLIF) and oblique lumbar interbody fusion (OLIF).

The interbody spacer is placed in the interdiscal space between adjacent vertebrae of the spine, resulting in spinal fusion of the adjacent vertebra wherein two or more vertebrae are joined together (fused) by way of the interbody spacer, sometimes with bone grafting, to form a single bone. The current standard of care for interbody fusion requires surgical removal of all or a portion of the intervertebral disc. After removal of the intervertebral disc, the interbody spacer is inserted in the space between the adjacent vertebrae.

Ideally, the interbody spacer should stabilize the intervertebral space and allow fusion of the adjacent vertebrae. Moreover, during the time it takes for fusion to occur, the interbody spacer body should have sufficient structural integrity to withstand the stress of maintaining the space without substantially degrading or deforming and have sufficient stability to remain securely in place prior to actual bone ingrowth fusion.

The interbody spacer is typically one piece that are assembled at the manufacturing stage. Many different size spacers are made, which results in a large inventory of plate/spacer body combinations, as well as large sterilization/shipping caddies to facilitate transfer of spacers large interbody spacers. In addition, typical interbody spacers require a secondary element to install the plate in-situ to inhibit fixation screw migration. This secondary action is time consuming and cumbersome when the surgical procedure is time sensitive.

Some prior art designs utilized titanium arms for distraction, this places a large amount of force on the PEEK spacer body, potentially damaging the spacer during assembly. This increased distraction force requires a large assembly tool to overcome the titanium arms and makes disassembly difficult.

It would be desirable to provide an interbody spacer with modularity and functionality to decreased inventory size.

SUMMARY

Disclosed is a spinal interbody spacer designed for interbody fusion, for example, oblique interbody fusion. Oblique interbody fusion is a minimally invasive procedure that involves the removal of damaged intervertebral disc and bone, and fusing of two adjacent spinal vertebrae. It adopts a lateral approach when compared to traditional methods of spinal fusion techniques, and in doing so, spares the disruption of major back muscles, ligaments and bones, and preserves back strength.

Oblique interbody fusion is recommended to treat abnormal spine curvature, fractured vertebrae, bulging discs, spine instability and spondylolisthesis (slipping out of vertebra). The procedure is performed under general anesthesia. Oblique interbody fusion is similar in approach to direct lateral interbody fusion (DLIF), but overcomes the drawback of DLIF in its ability to reach the last lumbar vertebra. This is made possible by approaching the vertebra obliquely and avoiding the pelvic bone. An incision is made in the side of your abdomen and soft tissues are carefully separated to reach the lumbar spine. The damaged vertebral bone or intervertebral disc is partially or totally removed. Bone graft or a suitable spacer is placed to maintain the intervertebral space and allow the bones to fuse. Screws, rods and plates may be used for additional support. The soft tissues are carefully repositioned and the incision closed.

The spinal interbody spacer includes a spinal spacer body and interchangeable screw fixation plates with a unique locking system that rigidly couples the spacer body and plate via a spring-loaded lock tab. The locking system include locking features designed to engage with the spring-loaded lock tab to lock the spinal spacer body and screw fixation plate together. The locking features are part of the spinal spacer body having tab distraction geometry and lock geometry. The tab distraction geometry includes a surface having an inclined or ramped portion and the lock geometry includes a tab recess or pocket in the surface. The distraction geometry is such that as the spinal spacer body and screw fixation plate are coupled, the spring-loaded lock tab will engage the inclined or ramped portion and push the spring-loaded lock tab in so that it can slide on the surface. Once the screw fixation plate and spacer body are completely joined, the spring-loaded lock tab reaches the tab recess or pocket, allowing the spring-loaded lock tab to return to its original position within the recess or pocket, thereby locking the spinal spacer body and screw fixation plate. The tab engaging the recess may provide an audible click sound the let the user know that the parts are joined and locked together.

BRIEF DESCRIPTION OF THE DRAWINGS

FIG. 5 shows a perspective view of the spinal spacer body.

FIG. 6 shows a sectional view at A-A of the spinal spacer body shown in FIG. 5.

FIG. 7 shows a sectional view at B-B of the spinal spacer body shown in FIG. 5.

FIG. 8 shows a perspective view of the screw fixation plate.

FIG. 9 is a cross-sectional view at C-C of the screw fixation plate.

FIG. 10 is a cross-sectional view at D-D of the screw fixation plate.

DETAILED DESCRIPTION

The invention is direct to a spinal interbody spacer that is a modular two-piece design comprising a spinal spacer body and an interchangeable screw fixation plate having an oblique or asymmetrical shape designed for oblique insertion delivery. The spinal spacer body and interchangeable screw fixation plates are designed to couple and lock together via a lock tab. The asymmetrical screw fixation plate is positioned near a corner of the implant to facilitate oblique insertion, and the angle for oblique insertion allows for an ALIF sized implant to be placed into a lumbar disc space between the psoas muscle and the great vessels, which reduces the risk of damage to the vessels. This procedure is commonly referred to as Oblique ALIF. It is important to note, however, that this lock tab connection could be used on an implant that is not oblique.

With this two-piece design, each of the components are provided in various sizes and configurations. This allows the surgeon to pick or choose the desired spacer body configuration and size for the patient, and then select the desired screw fixation plate configuration and join the spinal spacer body and screw fixation plate together. The spinal spacer body and screw fixation plate have engagement features that are configured to rigidly couple them together via the lock tab to form the spinal interbody spacer.

FIGS. 1A-1D show multiple configurations of a spinal interbody spacer 100 that is a modular two-piece design for oblique insertion to the spine. The spinal interbody spacer 100 includes a spinal spacer body 102 and a screw fixation plate 104 that are designed to couple and lock together via a unique lock tab having coupling features to rigidly affixed the spinal spacer body 102 to the screw fixation plate 104.

Figure 1A:
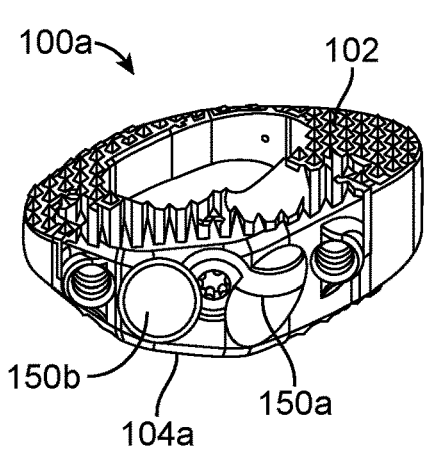
FIGS. 1A-1D show various configurations or variations of a modular spinal interbody spacer having a spinal spacer body coupled with different screw fixation plates.
Figure 1B:
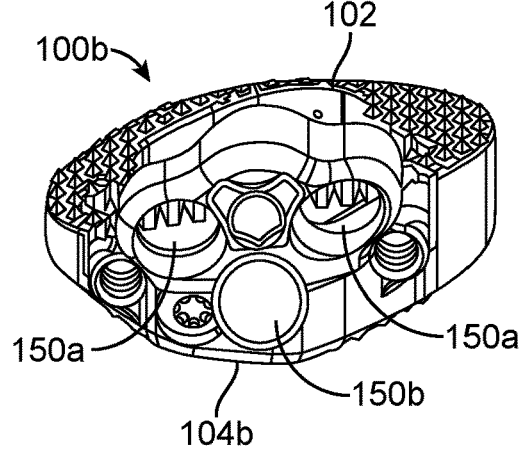
Figure 1C:
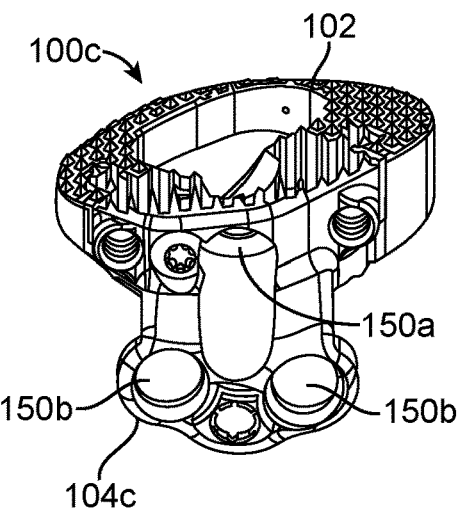
Figure 1D:
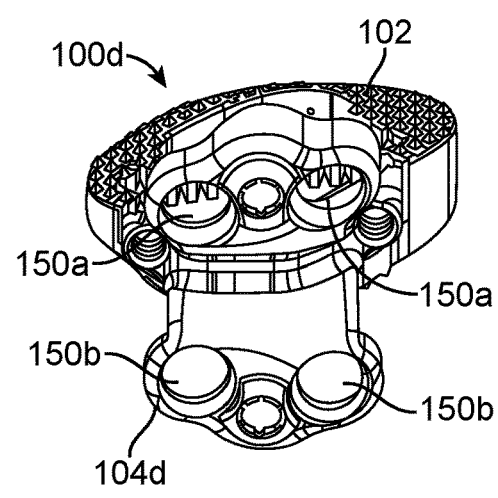

The figures show different configurations of the spinal interbody spacer 100 having a spinal spacer body 102 coupled with different variations of a screw fixation plate 104a, 104b, 104c, or 104d. The figures show examples of four configurations or variations of the modular spinal interbody spacer 100. FIG. 1A shows a spinal spacer body 102 coupled with a Zero screw fixation plate 104a. FIG. 1B shows a spinal spacer body 102 coupled with an upward Half screw fixation plate 104b. FIG. 1C shows a spinal spacer body 102 coupled with a downward Half screw fixation plate 104c. FIG. 1D shows a spinal spacer body 102 coupled with a Full screw fixation plate 104d. Each of the screw fixation plates 104 include at least two fastener holes 150, with an upward angle fastener hole 150a and a downward angle fastener hole 150b. The upward angle fastener hole 150a is configured to guide a bone engagement fastener upward to engage a vertebra above the modular spinal interbody spacer 100, and the downward angle fastener hole 150 is configured to guide a bone engagement fastener downward to engage a vertebra below the modular spinal interbody spacer 100.

Figure 2A:
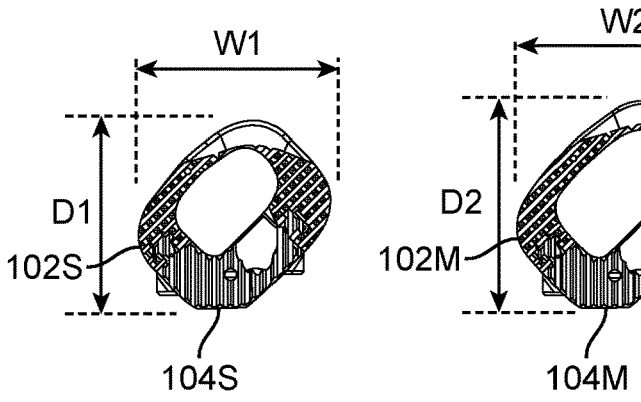
FIGS. 2A-2C show various configurations or variations of a spinal interbody spacer with different spinal spacer body footprints or configurations coupled with a screw fixation plate.
Figure 2B:
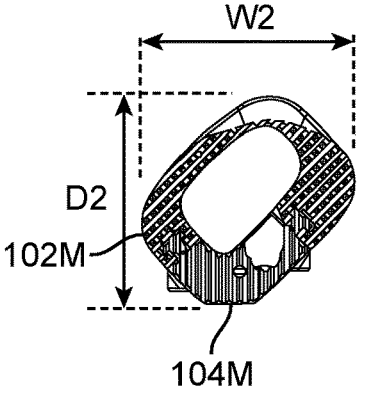
Figure 2C:
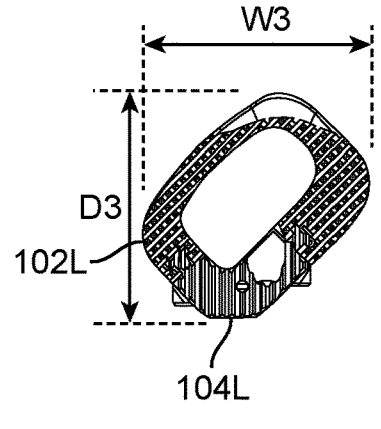

FIGS. 2A-2C show three configurations or variations of a spinal interbody spacer 100 comprising a three different footprints or configurations for the spinal spacer body 102 coupled with the screw fixation plate 104. The configurations may include various footprints having different widths W, depths D, heights and sagittal profiles. For example, FIG. 2A shows a small spinal spacer body 102S and small screw fixation plate 104S with a 24×30 mm footprint, FIG. 2B shows a medium spinal spacer body 102M and medium screw fixation plate 104M with a 26×34 mm footprint, and FIG. 2C shows a large spinal spacer body 102L and large screw fixation plate 104L with a 28×38 mm footprint. The modular spinal interbody spacers may be provided with different heights and sagittal profiles, such as five heights from 10 mm-18 mm @2 mm increments and three sagittal profiles, 7°, 12°, 30°.

Figure 3:
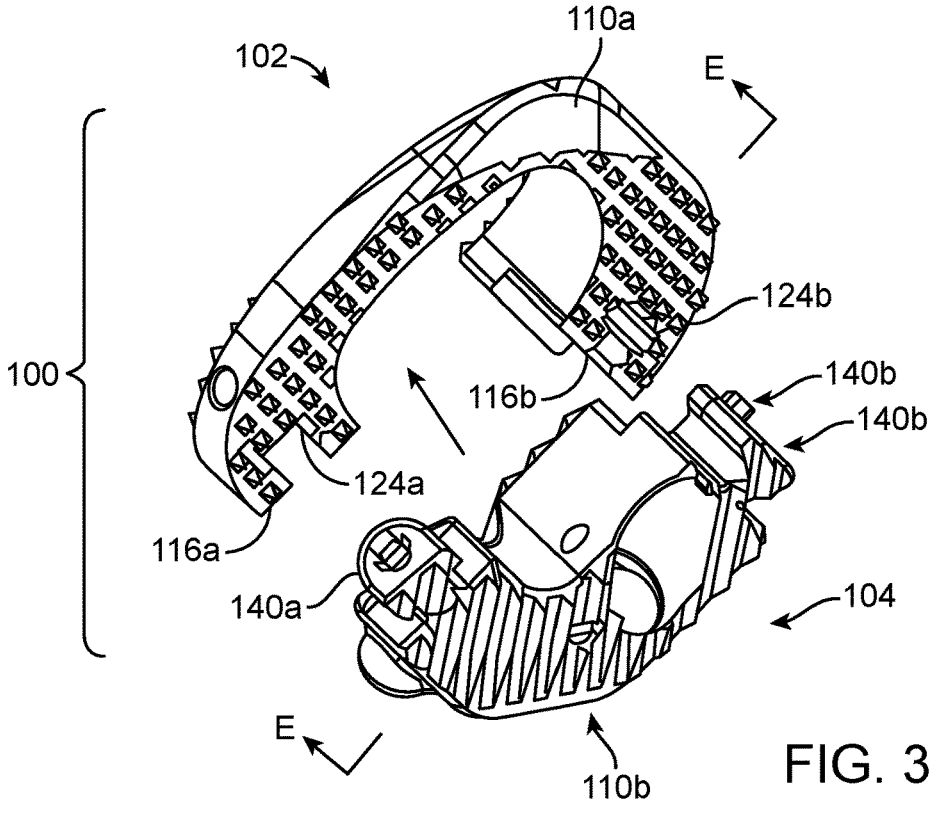
FIG. 3 shows an exploded perspective view showing one embodiment of a spinal interbody spacer

FIG. 3 is an exploded perspective view showing an anterior lumber interbody spacer 100 comprising a spinal spacer body 102 and a screw fixation plate 104 having coupling features to rigidly affixed the spinal spacer body 102 to the screw fixation plate 104.

Figure 4:
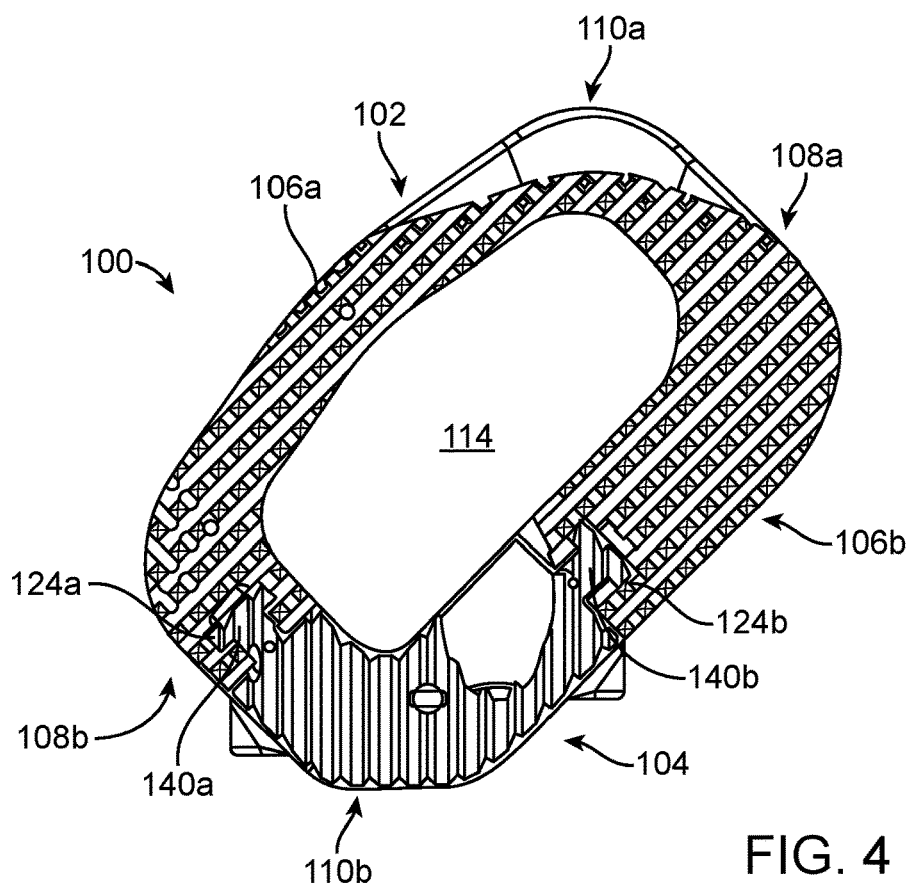
FIG. 4 shows the spinal spacer body and screw fixation plate coupled together.

FIG. 4 shows the spinal spacer body 102 and screw fixation plate 104 coupled together forming a generally rectangular shape with lateral sides 106a, 106b, 108a, 108b enclosing a central opening 114 with an asymmetrical distal end 110a and an asymmetrical proximal end 110b.

FIG. 5 shows a perspective view of the spinal spacer body 102, FIG. 6 is a cross-sectional view at A-A of the spinal spacer body 102, and FIG. 7 is a cross-sectional view at B-B of the spinal spacer body 102. In the embodiment shown, the spinal spacer body 102 is a generally J-shaped structure with a closed asymmetrical distal end 110a and an open asymmetrical proximal end 110b with open end walls 116a, 116b having alignment slots 124a, 124b. In the embodiment shown, the open-end walls 116a, 116b are 90 degrees apart. In other embodiments, the spinal spacer body 102 may have a different shape and the open-end walls may be more or less than 90 degrees apart. The spinal spacer body 102 may include a tapered portion on the asymmetrical distal end 110a of the spinal spacer body 102, opposite the open side, for easier insertion into the area between the upper and lower vertebra. The spinal spacer body 102 further includes an upper surface 118 and lower surface 120. The upper and lower surfaces 118, 120 may include teeth 122, such as pyramidal teeth. In some embodiments the surfaces may be roughened acid etch or blasted. The alignment slots 124a, 124b may be a vertical slot from the upper surface 118. In some embodiments, the spinal spacer body 102 may further include interior walls within central opening 114 forming multiple openings or pockets.

The alignment slots 124a, 124b may have tab distraction geometry and lock geometry. The tab distraction geometry includes a surface having an inclined or ramped portion 152 and the lock geometry includes a tab recess or pocket 158 in the surface. The distraction geometry is such that as the spinal spacer body and screw fixation plate are coupled, the inclined or ramped portion 152 will engage the alignment slots 124a, 124b and push the spring-loaded lock tab 126 in so that it can slide on the surface of the alignment slots 124a, 124b. Once the screw fixation plate and spacer body are completely joined, the spring-loaded lock tab reaches the tab recess or pocket, allowing the spring-loaded lock tab to return to its original position within the recess or pocket, thereby locking the spinal spacer body and screw fixation plate. The tab engaging the recess may provide an audible click sound the let the user know that the parts are joined and locked together.

FIG. 8 shows a perspective view of the screw fixation plate 104, FIG. 9 is a cross-sectional view at C-C of the screw fixation plate 104, and FIG. 10 is a cross-sectional view at D-D of the screw fixation plate 104. The screw fixation plate 104 is a generally L-shape with ends 130a, 130b and alignment protrusions 140a, 140b. The ends 130a, 130b and alignment protrusions 140a, 140b are configured to couple with the open ends 116a, 116b with alignment slots 124a, 124b of the spinal spacer body 102. The plate further includes an upper surface 134 and lower surface 136. The upper and lower surfaces 134, 136 may include teeth 138 as pyramidal teeth. In some embodiments the surfaces may be roughened acid etch or blasted. During assembly, the alignment protrusions 140a, 140b are inserted into the alignment slots 124a, 124b.

The screw fixation plate 104 includes locking mechanisms 132a, 132b on the alignment protrusions 140a, 140b. The locking mechanisms 132a, 132b include a spring-loaded lock tab 126. As the alignment protrusions 140a, 140b engage the alignment slots 124a, 124b, the spring-loaded lock tabs 126 engage the inclined or ramped portion 158 and are configured to be pushed in. Once the screw fixation plate 104 and spinal spacer body 102 are completely joined, the spring-loaded lock tab 126 reaches a tab recess or pocket 158 in the alignment slot allowing the spring-loaded lock tab 126 to return to its original position within the recess or pocket 158, thereby locking the spinal spacer body 102 and screw fixation plate 104. The spring-loaded lock tab 126 engaging the tab recess or pocket 158 may provide an audible click sound the let the user know that the parts are joined and locked together.

The locking mechanism 132a, 132b are positioned within a bore, hole, or slot 125 in the alignment protrusions 140a, 140b on the screw fixation plate 104. The locking mechanism 132a, 132b includes a spring 129 and the spring-loaded lock tab 126 slidable into the bore, hole, or slot 125. A retaining pin 128 is positioned in a slotted portion of the spring-loaded lock tab 126 to retain the spring-loaded lock tab 126 and limit the inward and outward travel. The retaining pin 128 may be made of nitinol and the spring 129 may be elgiloy. The spring-loaded lock tab 126 includes a ramped surface 127.

Figure 11:
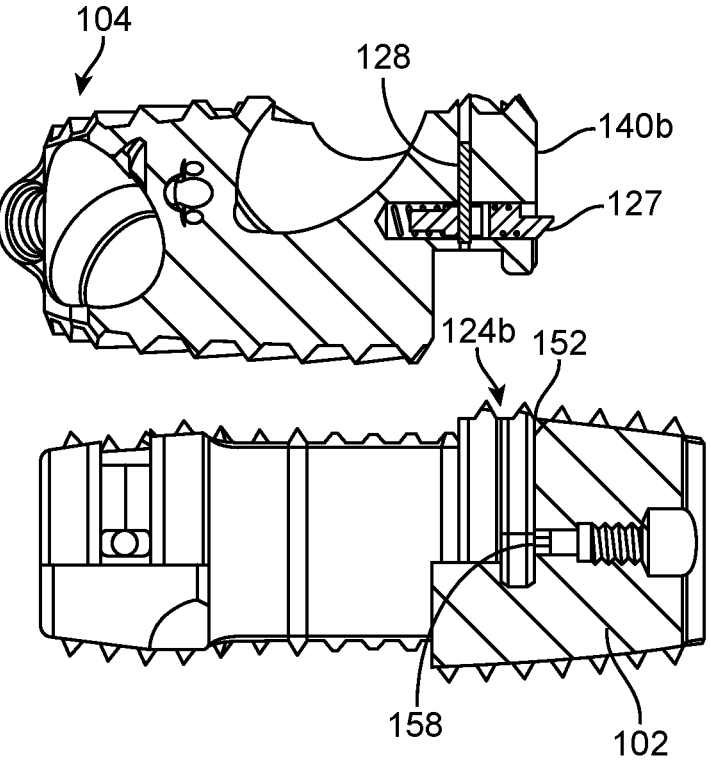
FIG. 11 is a cross-sectional view at E-E of FIG. 3 showing the assembly of the screw fixation plate into the spinal spacer body.
Figure 12:
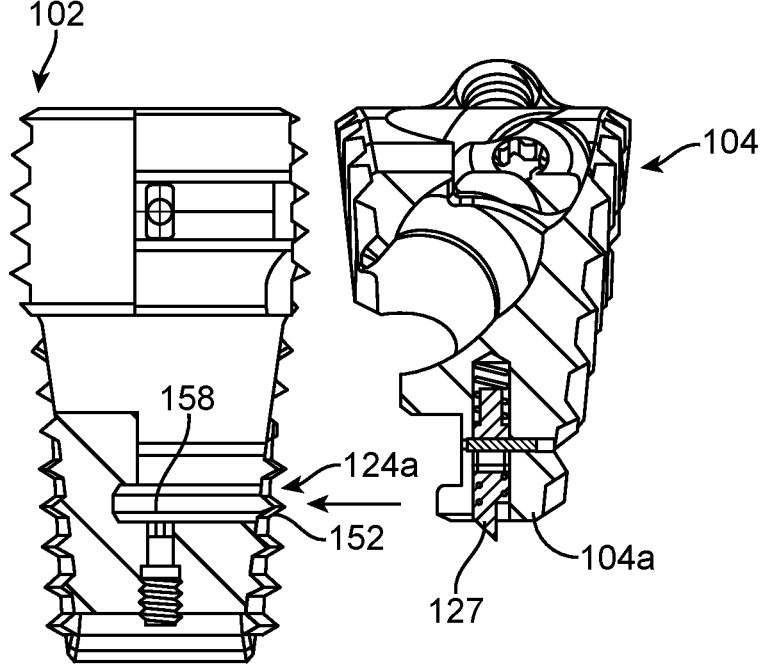
FIG. 12 is a cross-sectional view at F-F of FIG. 3 showing the assembly of the screw fixation plate into the spinal spacer body.

FIG. 11 is a cross-sectional view at E-E of FIG. 3 and FIG. 12 is a cross-sectional view at F-F of FIG. 3 showing the assembly of the screw fixation plate 104 into the spinal spacer body 102. The alignment protrusions 140a, 140b are inserted into alignment slots 124a, 124b.

The spinal spacer body 102 includes a tab compression portion and a tab locking portion. The tab compression portion includes an inclined or ramped portion 152 and the tab locking portion includes a tab engagement recess or tab lock recess 158. As the alignment protrusions 140a, 140b are slid into alignment slots 124a, 124b, the inclined or ramped portion 152 engages the ramped surface 127 of the spring-loaded lock tab 126 and forces the spring-loaded lock tab 126 to slide inward against the spring 129. Once the screw fixation plate 104 and spinal spacer body 102 are completely joined, the spring-loaded lock tab 126 reaches the lock geometry recess or pocket 158, allowing the spring-loaded lock tab 126 to return to its original position, thereby locking the screw fixation plate 104 to the spinal spacer body 102. The movement of the spring-loaded lock tab 126 into the geometry recess or pocket 158 may provide an audible click sound the let the user know that the parts are joined and locked together.

Figure 13:
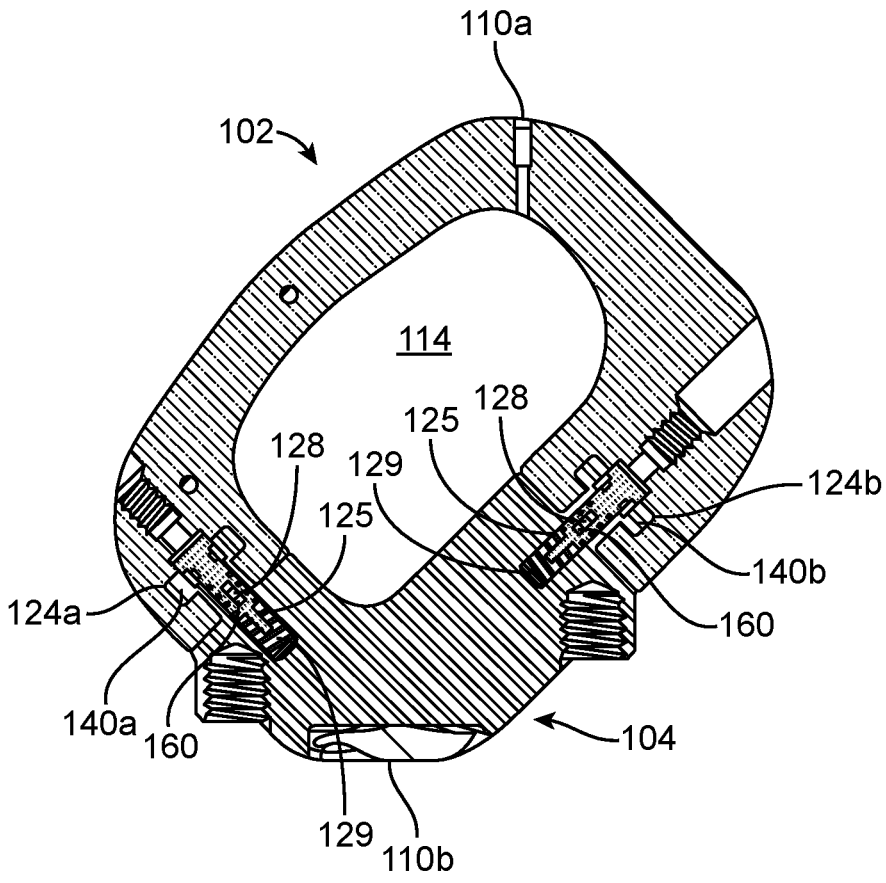
FIG. 13 is a sectional view showing the screw fixation plate coupled with the spinal spacer body.

FIG. 13 is a sectional view showing the screw fixation plate 104 coupled with the spinal spacer body 102. The spring-loaded lock tab 126 includes a slot 160 sized for the retaining pin 128. The slot 160 retains the spring-loaded lock tab 126 in the bore, hole, or slot 125 and limits the inward and outward movement. The spring-loaded lock tab 126 is also coupled to the spring 129. The spring 129 supplies a force to the spring-loaded lock tab 126 so that the spring-loaded lock tab 126 is naturally in the outward position. When the spring-loaded lock tab 126 engages the alignment slots 124a, 124b, the spring-loaded lock tab 126 compresses the spring 129. Once the spring-loaded lock tab 126 reaches the pocket 158, the spring forces the spring-loaded lock tab 126 to the outward position within the pocket 158, locking the screw fixation plate 104 with the spinal spacer body 102.

In some embodiments, the spinal interbody spacer 100 will utilize PEEK or titanium (TI) spinal spacer body 102 in conjunction with a titanium (TI) screw fixation plate 104.

The screw fixation plate 104 includes multiple fastener holes 150, with at least one fastener hole 150a tilted at an upward angle and at least one fastener hole 150b tilted at a downward angle. The upward angle fastener hole 150a allows a bone engagement fastener to engage a vertebra above the spinal interbody spacer 100, and the downward angle fastener hole 150b allows a bone engagement fastener to engage a vertebra below the spinal interbody spacer 100.

In the embodiments shown in FIGS. 1A-1D, the screw fixation plate Zero 104a includes two fastener holes, one fastener hole 150a tilted upward and the other fastener hole 150b tilted downward. The screw fixation plate upward Half 104b includes three fastener holes, two fastener holes 150a tilted upward and one fastener hole 150b tiled downward. The screw fixation plate downward Half 104c includes three fastener holes, one fastener hole 150a tilted upward and two fastener holes 150b tilted downward. The screw fixation plated Full 104d includes four fastener holes, two fastener holes 150a tilted upward and two fastener holes 150b tilted downward.

Figure 14:
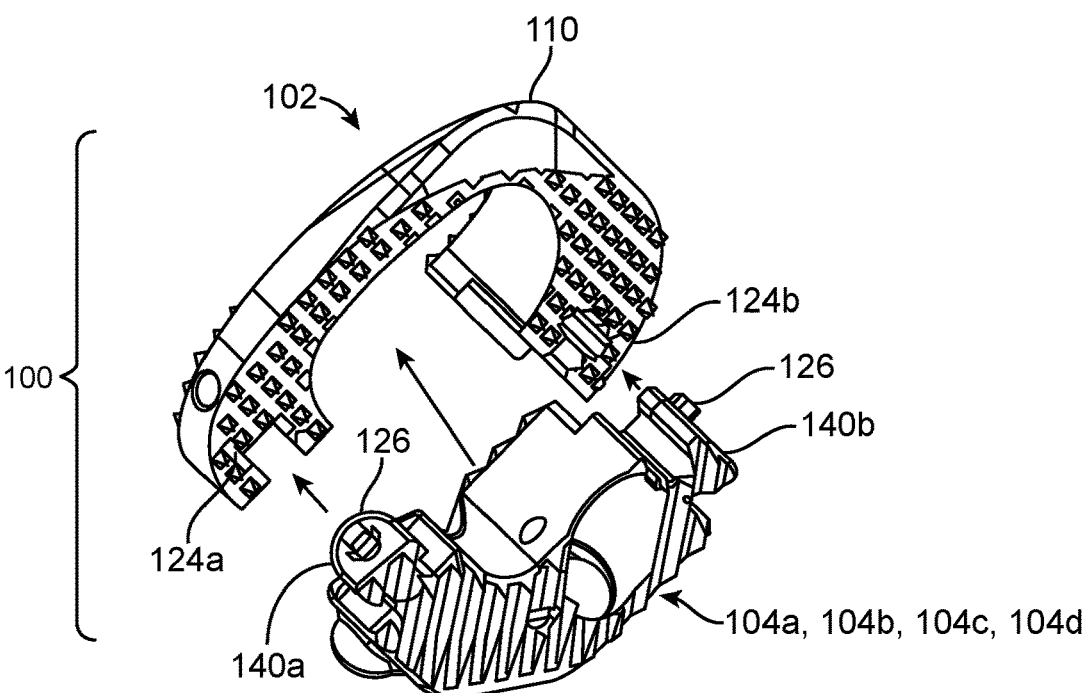
FIG. 14 shows assembly of the spinal interbody spacer that may be assembled on the back table in the operating room (OR).

FIG. 14 shows assembly of the spinal interbody spacer 100 that may be assembled on the back table in the operating room (OR). The spinal interbody spacer 100 can be assembled from a variety of screw fixation plates 104, such as 140a, 104b, 104c, or 104d and spinal spacer body 102, such as 102a, 102b, 102c, or 102d. To assemble the spinal interbody spacer 100, the alignment protrusions 140a, 140b of the screw fixation plate 104 are slid into the alignment slots 124a, 124b of the spinal spacer body 102 in a vertical direction. The geometry of the alignment protrusion 140 is such that it will force the spring-loaded lock tab 126 to distract into a bore, hole, or slot 125 in the spacer body. Once the screw fixation plate 104 has been sufficiently inserted into the spinal spacer body 102, the lock geometry 158 on the screw fixation plate 104 will allow for the spring-loaded tab 126 to return to its original position in pocket 158, thereby locking the screw fixation plate 104 with the spinal spacer body 102. Engaging the recess 158 may provide an audible click sound the let the user know that the parts are joined and locked together.

Figure 15:
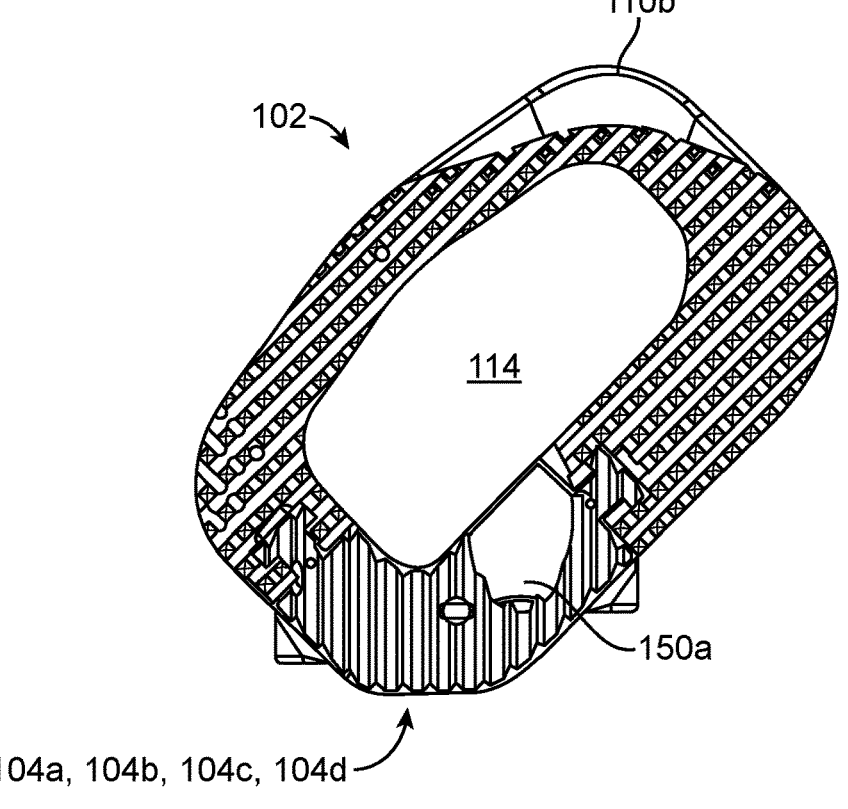
FIG. 15 shows the spinal interbody spacer in the implanted configuration.

FIG. 15 shows the spinal interbody spacer 100 in the implanted configuration. The screw fixation plate 104 includes two more fastener holes 150 sized to receive bone engagement fasteners configured to anchor the spinal interbody spacer 100 between two vertebrae of the spine.

Figure 16:
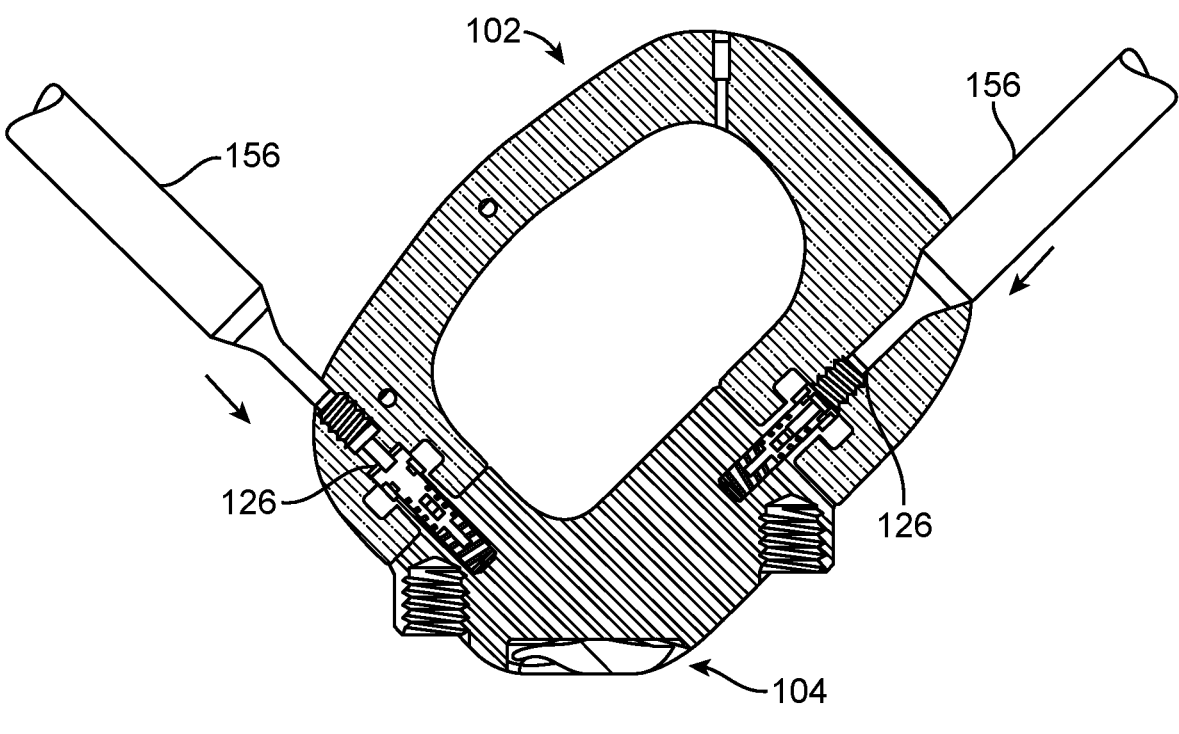
FIG. 16 is a top sectional view showing use of the implant disassembly tool.
Figure 17:
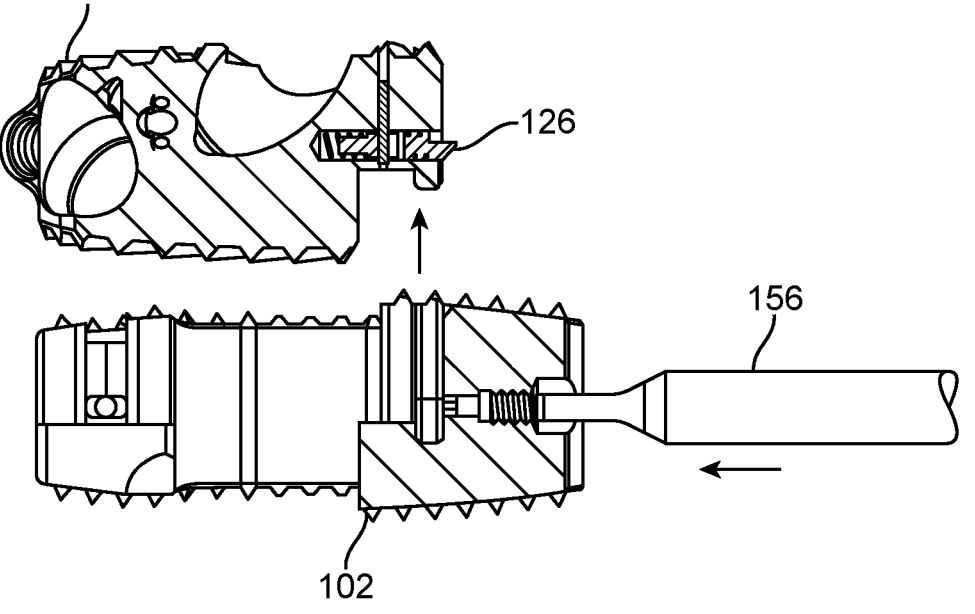
FIG. 17 is a side sectional view at G-G of FIG. 16.

FIG. 16 is a top sectional view showing use of the implant disassembly tool 156. FIG. 17 is a side sectional view at G-G of FIG. 16 showing the separation of the screw fixation plate 104 from the spinal spacer body 102. An implant disassembly tool 156 that is used to disengage the spring-loaded lock tab 126. The implant disassembly tool 156 is inserted through a hole in the screw fixation plate and pushes the spring-loaded lock tab 126 into the bore, hole, or slot 125 to disengage the screw fixation plate 104 from the spinal spacer body 102.

Figure 18A:
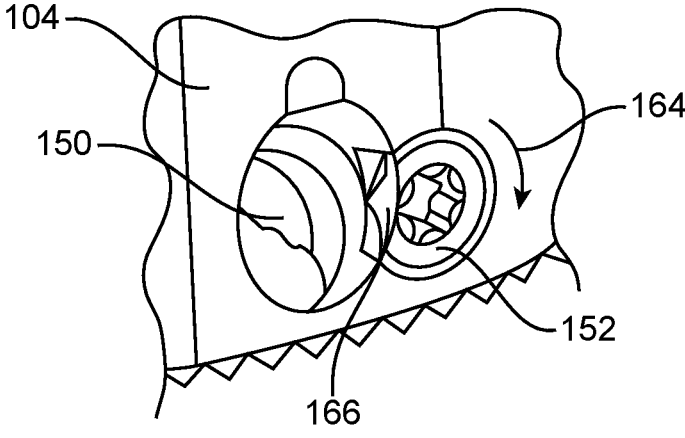
FIGS. 18A, 18B show embodiments of bone screw locking feature.
Figure 18B:
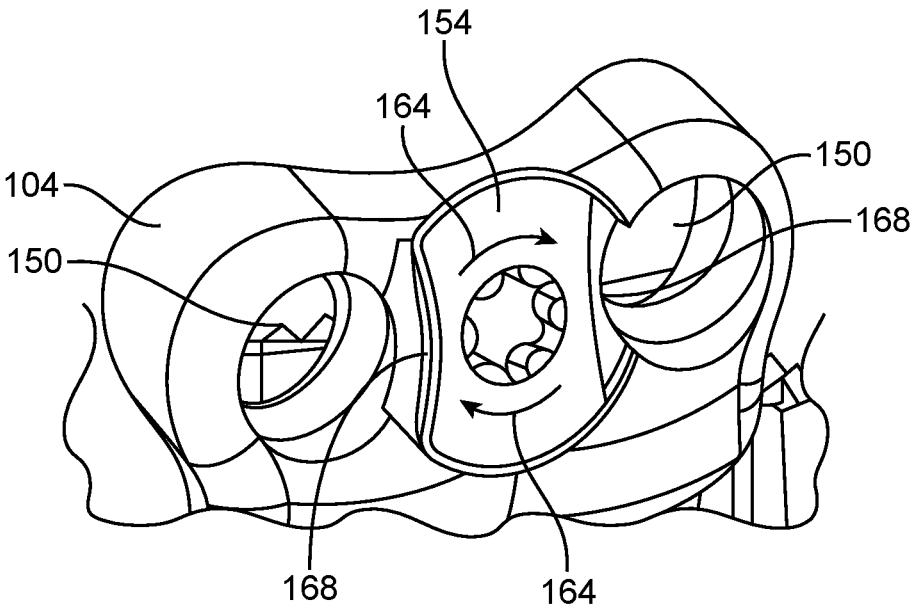

FIGS. 18A, 18B show embodiments of bone screw locking feature, such as a single hole locking feature 152 and a double hole locking feature 154. The bone screw locking feature is designed to allow passage of the bone engagement fastener into the fastener hole 150, then rotate 164 to cover a portion of the fastener hole 150 to prevent the bone engagement fastener from withdrawing from the fastener hole 150. FIG. 16A shows single hole locking feature 154 positioned near the fastener hole 150. The locking feature 154 has a cut-out portion 166 that allows a bone engagement fastener to pass into the fastener hole 150. The locking feature 154 is rotated 164 to cover part of the fastener hole 150. FIG. 16B shows double hole locking feature 154 positioned between two fastener holes 150. The locking feature 154 has a two cut-out portions 168 that allows bone engagement fasteners to pass into the fastener holes 150. The locking feature 154 is rotated 164 to cover part of the fastener hole 150 to prevent the bone engagement fastener from backing out.

The present invention requires relatively small amounts of assembly force due to the elasticity of the spring-loaded tab and spring, in addition, the tab can be easily distracted utilizing a secondary instrument, allowing for simple and fast implant disassembly.

Example embodiments of the methods and systems of the present invention have been described herein. As noted elsewhere, these example embodiments have been described for illustrative purposes only and are not limiting. Other embodiments are possible and are covered by the invention. Such embodiments will be apparent to persons skilled in the relevant art(s) based on the teachings contained herein. Thus, the breadth and scope of the present invention should not be limited by any of the above-described exemplary embodiments but should be defined only in accordance with the following claims and their equivalents.

The invention claimed is:

1. A modular interbody spacer for placement between adjacent vertebrae comprising:

a spacer body having upper and lower vertebrae engagement surfaces with a closed distal end and an open proximal end, the open proximal end having an asymmetrical shape with spacer body end walls with spacer body alignment slots having a spacer body alignment slot surface with a spacer body alignment slot recess or pocket;

an asymmetrical screw fixation plate having upper and lower bone vertebrae surfaces with screw fixation plate end walls with screw fixation plate alignment protrusions with a screw fixation plate bore or hole, the screw fixation plate configured to couple with the spacer body end walls and the screw fixation plate alignment protrusions configured to slidably couple with the spacer body alignment slots; and a locking mechanism slidably positioned within the screw fixation plate bore or hole of the screw fixation plate alignment protrusions, the locking mechanism having a retractable lock tab configured to retract into the screw fixation plate bore or hole during engagement with the spacer body alignment slot surface, and extend from the screw fixation plate bore or hole during engagement with the spacer body alignment slot recess or pocket to lock the screw fixation plate and the spacer body together.

2. The modular interbody spacer of claim 1, wherein:

the spacer body is selected from a group of interchangeable spacer bodies; and the screw fixation plate is selected from a group of interchangeable asymmetrical screw fixation plates configured to fit the asymmetrical open proximal end of the spacer body.

3. The modular interbody spacer of claim 1, wherein the spacer body alignment slot surface of the spacer body alignment slots include an inclined or ramped portion configured to engage and move the retractable lock tab inward in the screw fixation plate bore or hole of the screw fixation plate alignment protrusions.

4. The modular interbody spacer of claim 1, wherein the retractable lock tab includes a spring-loaded lock tab and spring.

5. The modular interbody spacer of claim 4, wherein the spacer body alignment slot recess or pocket of the spacer body alignment slots include a spacer body tab engagement recess configured to engage and allow the spring-loaded lock tab and spring to move outward from the screw fixation plate bore or hole of the screw fixation plate alignment protrusions and lock the spring-loaded lock tab.

6. The modular interbody spacer of claim 5, wherein the spring-loaded lock tab includes a lock tab slotted portion and a screw fixation plate retaining pin positioned in the lock tab slotted portion to retain the spring-loaded lock tab and limit inward and outward travel.

7. The modular interbody spacer of claim 1, wherein the screw fixation plate includes a screw fixation plate hole configured to receive a disassembly tool to disengage the locking mechanism.

8. A modular interbody spacer for placement between adjacent vertebrae comprising:

a spacer body having upper and lower vertebrae engagement surfaces with a closed distal end and an asymmetrical open proximal end, the open proximal end having spacer body end walls with spacer body alignment slots having a spacer body alignment slot surface with a spacer body alignment slot recess or pocket;

an asymmetrical screw fixation plate having upper and lower bone vertebrae surfaces and screw fixation plate alignment protrusions configured to slidably couple with the spacer body alignment slots, each screw fixation plate alignment protrusion having a screw fixation plate bore or hole;

a locking mechanism having a retractable lock tab slidably positioned in the screw fixation plate bore or hole of the screw fixation plate alignment protrusions, the retractable lock tab configured to retract into the screw fixation plate bore or hole during engagement with the spacer body alignment slot surface of the spacer body alignment slots, and extend from the screw fixation plate bore or hole during engagement with the spacer body alignment slot recess or pocket of the spacer body alignment slots.

9. The modular interbody spacer of claim 8, wherein:

the spacer body is selected from a group of interchangeable spacer bodies; and the screw fixation plate is selected from a group of interchangeable asymmetrical screw fixation plates configured to fit the asymmetrical open proximal end of the spacer body.

10. The modular interbody spacer of claim 8, wherein the spacer body and screw fixation plate are locked together when the retractable lock tab engages the spacer body alignment slot recess or pocket of the spacer body alignment slots.

11. The modular interbody spacer of claim 8, wherein the spacer body alignment slot surface of the spacer body alignment slots include a tab compression portion having an inclined or ramped portion configured to engage and move the retractable lock tab inward in the screw fixation plate bore or hole of the screw fixation plate alignment protrusions.

12. The modular interbody spacer of claim 8, wherein the spacer body alignment slot surface of the spacer body alignment slots include a tab locking portion having a spacer body tab engagement recess configured to engage and allow the retractable lock tab to move outward from the screw fixation plate bore or hole of the screw fixation plate alignment protrusions and lock the retractable lock tab.

13. The modular interbody spacer of claim 8, wherein the locking mechanism is a spring-loaded lock tab with a spring that includes a lock tab slotted portion and a screw fixation plate retaining pin positioned in the lock tab slotted portion to retain the spring-loaded lock tab and limit inward and outward travel.

14. The modular interbody spacer of claim 8, where the screw fixation plate includes a screw fixation plate hole configured to receive a disassembly tool to disengage the locking mechanism.

* * * * *